US012721521B2

(12) United States Patent
Marcacci

(10) Patent No.: US 12,721,521 B2
(45) Date of Patent: Sep. 1, 2026

(54) MULTIFUNCTIONAL OPHTALMIC APPARATUS

(71) Applicant: COSTRUZIONI STRUMENTI OFTALMICI C.S.O. S.R.L., Scandicci (IT)

(72) Inventor: Matteo Marcacci, Barberino Tavarnelle (IT)

(73) Assignee: COSTRUZIONI STRUMENTI OFTALMICI C.S.O. S.R.L., Scandicci (IT)

(*) Notice: Subject to any disclaimer, the term of this patent is extended or adjusted under 35 U.S.C. 154(b) by 410 days.

(21) Appl. No.: 18/255,242

(22) PCT Filed: Dec. 1, 2021

(86) PCT No.: PCT/IB2021/061163

§ 371 (c)(1),
(2) Date: May 31, 2023

(87) PCT Pub. No.: WO2022/118206

PCT Pub. Date: Jun. 9, 2022

(65) Prior Publication Data

US 2024/0090767 A1 Mar. 21, 2024

(30) Foreign Application Priority Data

Dec. 2, 2020 (IT) ........................ 102020000029393

(51) Int. Cl.
*A61B 3/18* (2006.01)
*A61B 3/00* (2006.01)
(Continued)

(52) U.S. Cl.
CPC .............. *A61B 3/18* (2013.01); *A61B 3/0083* (2013.01); *A61B 3/111* (2013.01); *A61B 3/152* (2013.01)

(58) Field of Classification Search
CPC ......... A61B 3/18; A61B 3/0083; A61B 3/111; A61B 3/152
(Continued)

(56) References Cited

U.S. PATENT DOCUMENTS 3,201,795 A 8/1965 Cuppers et al.
2013/0271727 A1* 10/2013 Akiba .................... A61B 3/152 351/205
(Continued)

FOREIGN PATENT DOCUMENTS

GB 862730 A 3/1961
IT 201800008236 A1 2/2020

OTHER PUBLICATIONS

International Search Report and Written Opinion for Corresponding International Application No. PCT/IB2021/061163, 13 pages, Mar. 16, 2022.
(Continued)

*Primary Examiner* — Bumsuk Won
*Assistant Examiner* — Rahman Abdur
(74) *Attorney, Agent, or Firm* — LUCAS & MERCANTI, LLP

(57) ABSTRACT

The present invention relates to the field of diagnostic equipment in the ophthalmic field, and more precisely has as its object a multifunctional apparatus capable of performing measurements, examinations and even operations of various kinds on the eye of a patient.

12 Claims, 5 Drawing Sheets

(51) Int. Cl.
*A61B 3/11* (2006.01)
*A61B 3/15* (2006.01)

(58) Field of Classification Search
USPC .......................................................... 351/204
See application file for complete search history.

(56) References Cited

U.S. PATENT DOCUMENTS

| | | | | |
|---|---|---|---|---|
| 2013/0339043 | A1 | 12/2013 | Bakar et al. | |
| 2014/0022351 | A1* | 1/2014 | Cho ....................... | H04N 23/69 348/240.99 |
| 2017/0347872 | A1* | 12/2017 | Ozaki .................. | A61B 3/0083 |
| 2019/0313896 | A1 | 10/2019 | Lane et al. | |

OTHER PUBLICATIONS

International Preliminary Report On Patentability for Corresponding International Application No. PCT/IB2021/061163, 27 pages, Feb. 17, 2023.

* cited by examiner

MULTIFUNCTIONAL OPHTALMIC APPARATUS

CROSS-REFERENCE TO RELATED APPLICATIONS

This application is a 371 of PCT/IB2021/061163, filed Dec. 1, 2021, which claims the benefit of Italian Patent Application No. 102020000029393, filed Dec. 2, 2020.

TECHNICAL FIELD OF THE INVENTION

The present invention relates to the field of ophthalmic diagnostic equipment, and more specifically to a multifunctional apparatus for performing measurements, examinations and operations of various kinds on the eye of a patient.

BACKGROUND OF THE INVENTION

Solutions are known that in the context of a single ophthalmic equipment allow to perform, through different devices, but in a substantially concurrent way (i.e. in successive steps of a single examination session) measurements or examinations related to different characteristics of an eye. To this end, the apparatus can be equipped with a device for measuring intraocular pressure (tonometer), and with a different examination device (a corneal topographer, a tomograph, etc.) designed to take action in respective successive steps on an eye of a patient, to perform measurements or detections, in a mutually coordinated/correlated manner or independently from each other.

In carrying out the measurements within the same session, with the patient stationary in the examination position, there is obviously the problem of moving the devices in such a way as to place them on the optical axis of the eye under examination, possibly and advantageously without repeating the alignment procedures and thus potentially compromising the accuracy and consistency of the measurements, or prolonging the examination session with consequent discomfort for the patient.

In some known solutions, e.g., those shown in documents U.S. Pat. No. 3,201,795 and GB862730, provision is made for mounting a plurality of ophthalmic instruments or devices on a single rotatable carousel system, with the instruments being able to come into action one after the other as a result of the rotation of the carousel, which aims to simplify and speed up the adjustment steps of individual instruments as compared to structures in which they are autonomously and independently supported. However, the possibilities of adjustment remain reduced and have definite limits of accuracy.

SUMMARY OF THE INVENTION

Taking into account these problems, but more generally with the object to provide an appreciable alternative to the known solutions, the present applicant has conceived a new configuration of multifunctional apparatus which, in addition to fully effectively satisfying the needs related to the transition phase between devices and their alignment, overcomes some limitations of the apparatuses so far proposed and available on the market, as regards the combination of the various functionalities, the compatibility of the related optical paths, the handling constraints according to the various directions in space.

Such a multifunctional ophthalmic apparatus according to the present invention has the essential features set forth in the first of the appended claims. Other optional features are the subject of the secondary claims.

BRIEF DESCRIPTION OF THE DRAWINGS

The features and advantages of the multifunctional ophthalmic apparatus according to the present invention will result more clearly from the following description of an embodiment thereof, made by way of example and not limitative, with reference to the attached drawings in which.

DETAILED DESCRIPTION OF THE INVENTION

With reference to the above figures, an apparatus according to the invention, in an embodiment comprises a base 1 suitable for direct or indirect resting, through a face defining a resting plane 1*a*, on a horizontal surface such as that made available by a desk or even by a floor, supporting a foot 2 and a support column 3 rising from the foot 2. The assembly of these components forms a frame 10 of the apparatus.

A Cartesian system XYZ is defined by said resting plane 1*a* (depth direction X and laterality direction Y parallel to said plane) and a third, height, direction Z, along which the column 3 is developed and elevated.

The frame 10, in the present example by means of the column 3, rotatably supports, around an axis of rotation X' parallel to the depth direction X, an instrument-bearing carousel 4, for example substantially circular, which on a front surface thereof 4*a*, intended to face the head C of the patient under examination, and parallel to the directions YZ, supports a plurality of measuring or examining devices or instruments, for example three as in the illustrated example, denoted at 51, 52, 53, each defining an optical axis L1, L2, L3 parallel to the rotation axis X' and possibly (but not necessarily) at the same radial distance from the latter. The optical axis Ln of each instrument is therefore suitable to be placed in alignment, following the adjustment movements and the rotation in discrete steps of the carousel 4, with the optical axis of the eye E of the patient to be examined.

Figure 1:
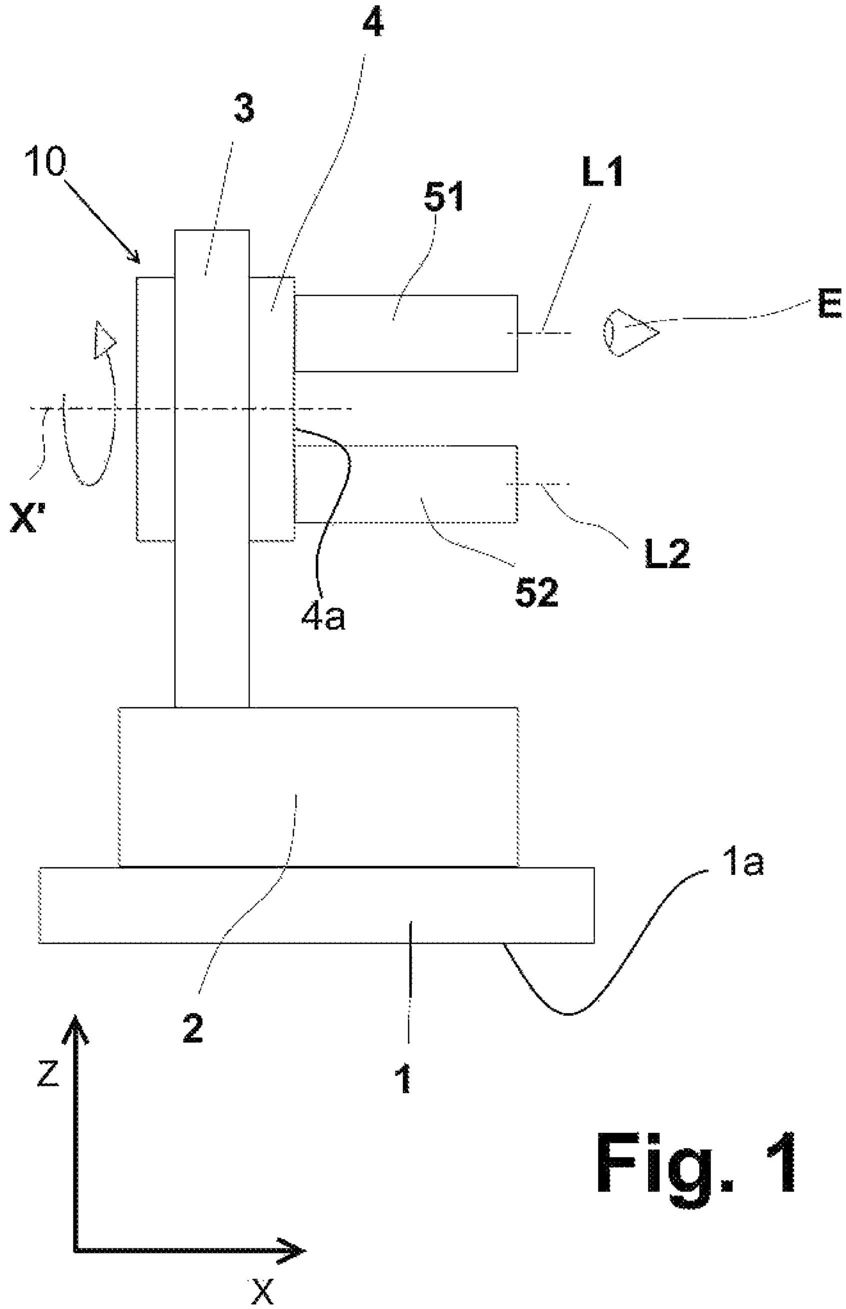
FIG. 1 is a side view of the apparatus represented in schematic and conceptual form to roughly highlight its architecture.
Figures 2, 3:
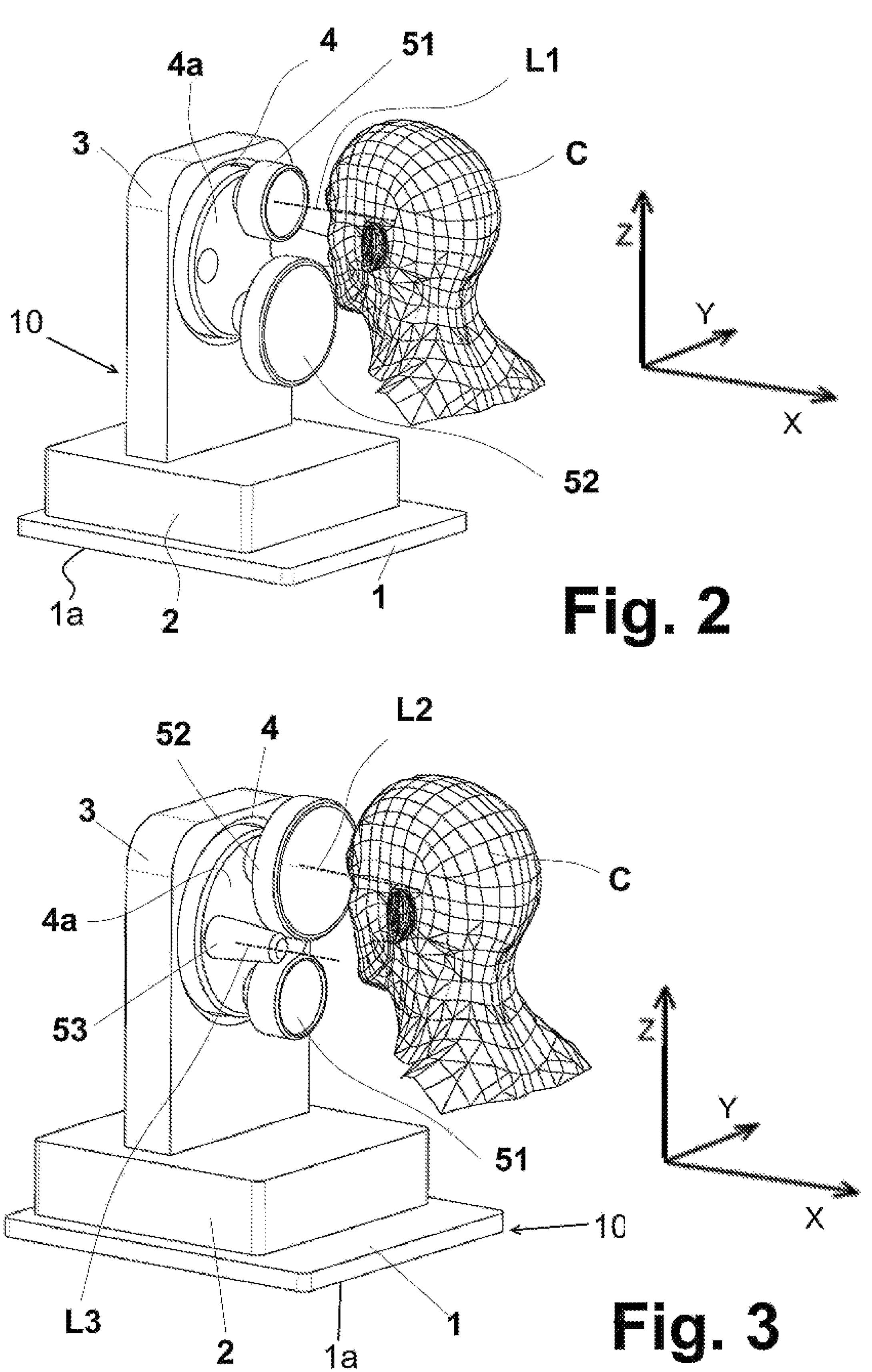
FIGS. 2 and 3 are axonometric views of the equipment in a more realistic form, although still schematic, in two different operating positions of an examination session, with also represented the head of a patient under examination.
Figure 4:
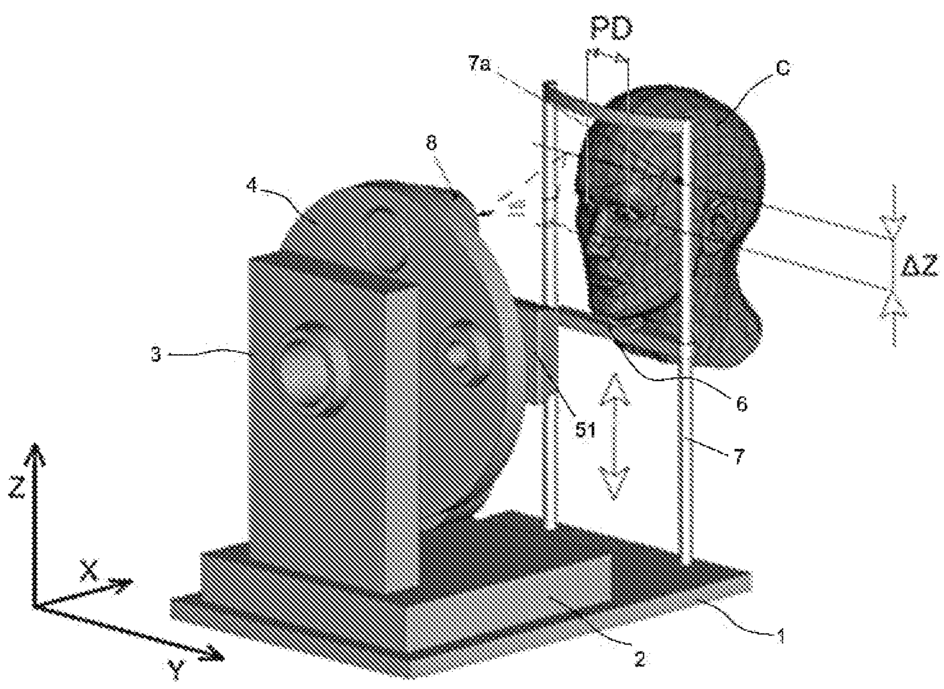
FIG. 4 shows again axonometrically an apparatus similar to the previous ones, represented constructively, in a less schematic way and with additional instrumentation, in examination set-up on the head of a patient, to better highlight some operational and adjustment parameters of the apparatus.
Figure 5:
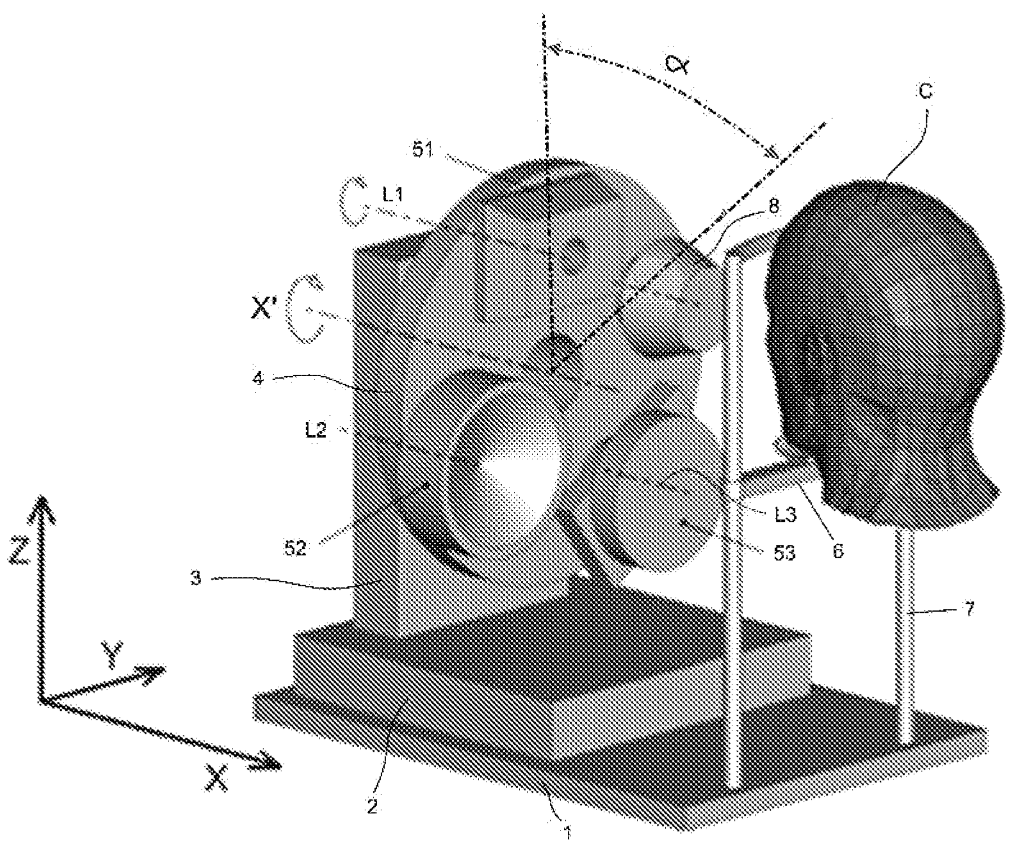
FIG. 5 is again an axonometric view of the equipment provided with the same intent as that of FIG. 4, from a different angle.
Figure 8:
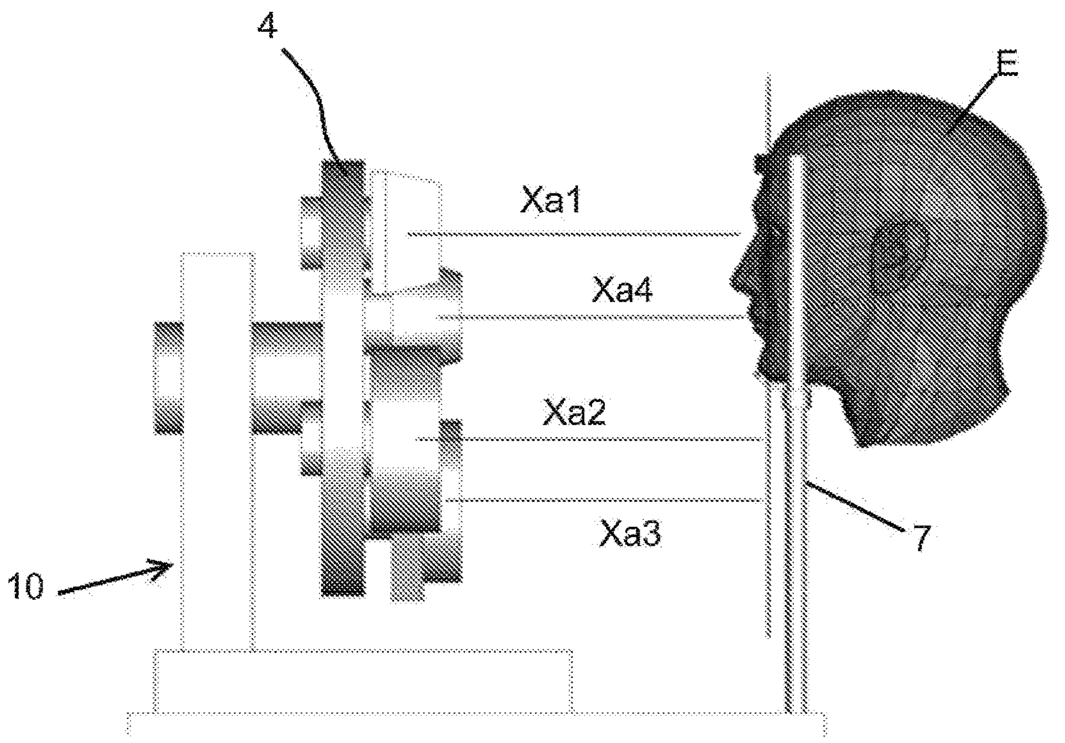
FIG. 8 shows the equipment in the version of FIGS. 4 and 5, in a side view.
Figure 9:
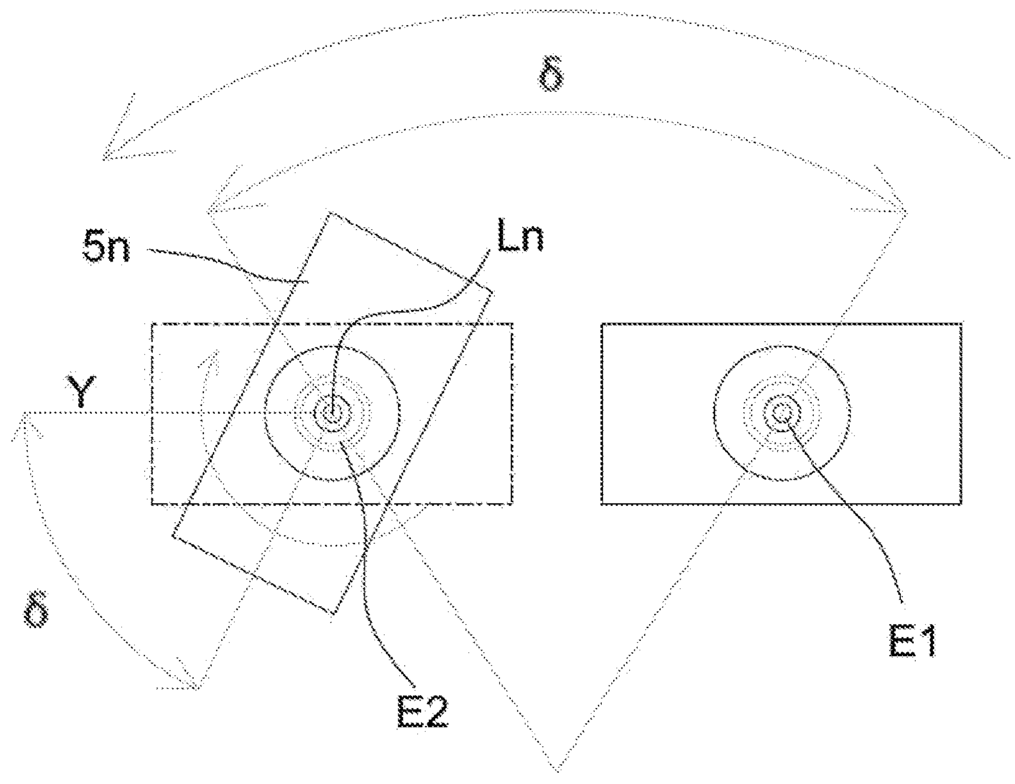
FIG. 9 is a schematic representation similar to that of FIG. 7, illustrating the transition of an instrument or head from an examination condition of a first eye to an examination condition of a second eye of the same patient.

For the rest and reference of the patient's head C, as depicted in FIGS. 4, 5 and 8, but omitted in FIGS. 1 to 3, there is provided a chin rest 6 which is supported in turn in a mobile manner (with motorization) along the height direction Z by a chin rest rail 7 which rises from the base 1. The rail has a reference mark 7*a* for alignment in height of the patient's eyes.

According to the invention, the axis of rotation X' of the carousel is therefore horizontal when the apparatus is in its operating position. In addition, the rotation axis of the carousel 4 is movably supported by the frame 10 with respect to at least the height direction Z, so as to allow adjustment along this direction. The adjustment motion is in the illustrated example obtained by displacement of the column 3 relative to the foot 2, but other equivalent solutions may be provided.

Also in the context of the present example, motorized actuation means are arranged in foot 2, of obvious nature in themselves and not represented or described in detail, capable of moving the column (or equivalently the rotation axis of the carousel) not only according to the height direction Z, but also according to an adjustment in the depth direction X, while according to the laterality direction Y the rotation axis is preferably fixed.

The number n of instruments or devices 5*n* may in general be different from three, and therefore less or more compatibly with the available space and the relative encumbrances. The devices, or at least the slots provided on the carousel for their assembly (not necessarily all occupied) can be equally spaced along the perimeter of the carousel itself, with an angular distance at the center of the axis of rotation equal to 360°/n. But more generally, and in some cases advantageously where required by the needs of balance of the overall dimensions and weights according to the type of instruments used, the angle in question may vary within the set, and then one can have different values between different pairs of consecutive instruments.

In any case, this angle will correspond to the angular step (constant or not) of rotation of carousel 4 to bring the different devices from time to time in the position of alignment with the patient's eye, and therefore in the position of the examination that is the responsibility of the device from time to time concerned.

All the drive systems, including those already mentioned for the adjustment directions and the one clearly arranged inside column 3 to impart rotation to carousel 4, as well as the command and control system, can be directly implemented on the basis of the common knowledge in the field without the need for a detailed description. The same applies to any accessory components which, depending on the devices or instruments employed, should become necessary to ensure the functionality of the single instrument, of which the component mounted on the carousel can only be the measuring or capturing head, all again on the basis of the known reference technology for that specific instrument.

The principle operating behavior of the apparatus can be inferred with reference first to FIGS. 2 and 3. By rotating the carousel 4, the first device or instrument 51 to be used in the first phase of the examination session is initially placed in the examination position, which tends to be the twelve o'clock position, with the patient's head C placed in the examination set-up.

With the aid of the motion of the carousel at least along the Z-height direction (as will be better explained below), the optical axis L1 of the first instrument or measuring head 51 is aligned with the axis of the eye (FIG. 2).

Once the examination has been performed with the first instrument 51, the rotation of carousel 4, around the rotation axis X', is commanded by the angular step necessary to bring a second instrument 52 into the examination position, which, in the case of equidistant placement of its optical axis L2 with respect to the rotation axis, and keeping the patient still, does not need to be the subject of a new and further alignment adjustment (FIG. 3).

The procedure can then stop or be repeated in a similar way for device 53 or 5*n*, again without resorting to a new alignment between the Ln axis of the nth device and the patient's optical axis, with what follows in terms of consistency and speed of the examination session.

Having said this in substantially schematic and conceptual terms, with more specific reference to FIGS. 4 to 9, the methods of use of the apparatus can be further detailed in the following terms.

Advantageously, in addition to the true and proper measuring instruments 5*n*, the apparatus according to the present invention may comprise, as precisely represented herein, image acquisition means for facial recognition, such as a video camera 8, again mounted on the front surface 4*a* of the carousel 4, and in a position radially and circumferentially consistent with that of the instruments (in practice, if a number n of actual measuring instruments are provided, the camera takes the (n+1)th place in a carousel with n+1 stations).

By means of the video camera 8, and in particular by processing the images acquired by it, the control system of the equipment is able to record the Z and Y coordinates of the eyes, from which the differential height ΔZ of the eye(s) with respect to the sign 7*a*, and the interpupillary distance PD are retrieved.

The chin rest 6 is first used and checked for a rough adjustment of the height positioning of the patient's head so that the eye is in a position that is surely reachable by the measuring instrumentation and the patient is in a comfortable position. To this purpose, the movement of the chin rest is controlled so that the patient's eye is in the vicinity of mark 7*a* on track 7 (FIG. 4). Being it known the value ΔZ, the chin rest is then finely shifted for a corresponding distance to ensure that the eye is perfectly aligned with the mark, as shown in FIG. 4.

Contrary to what happens in known devices, this adjustment through the chin rest is only a first rough adjustment, the fine adjustment along the height direction Z being, as further understood hereafter, achieved through the movements of the main part of the apparatus (carousel and its frame).

Figure 6:
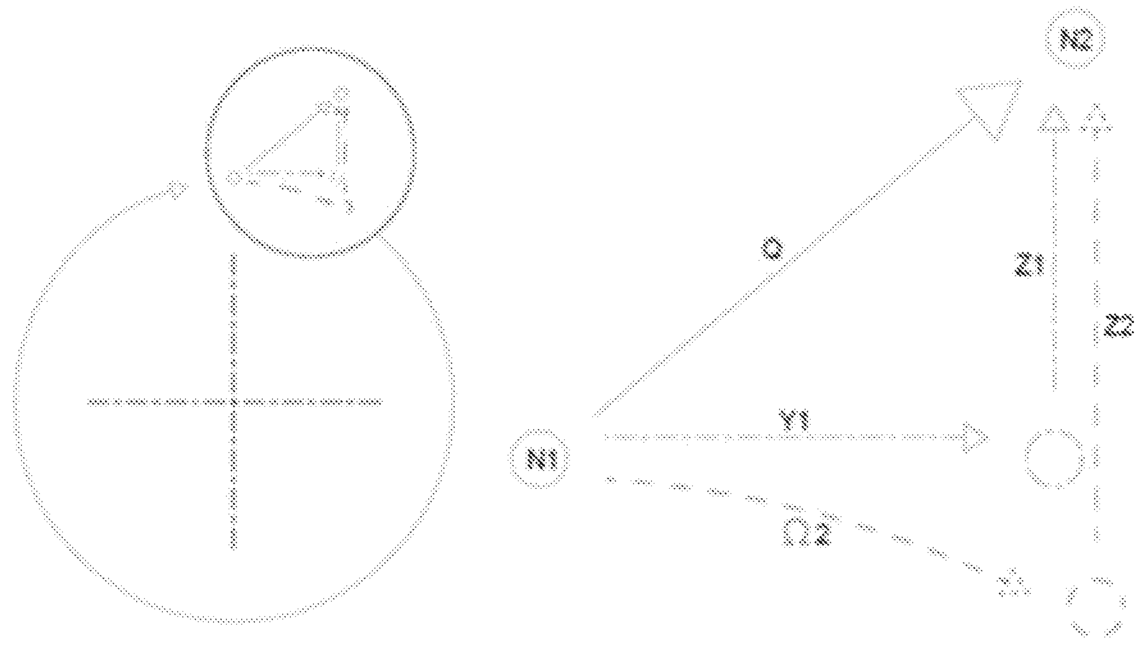
FIG. 6 is a diagram illustrating a breakdown of the movements of the equipment in a positioning phase with respect to a patient's eye.
Figure 7:
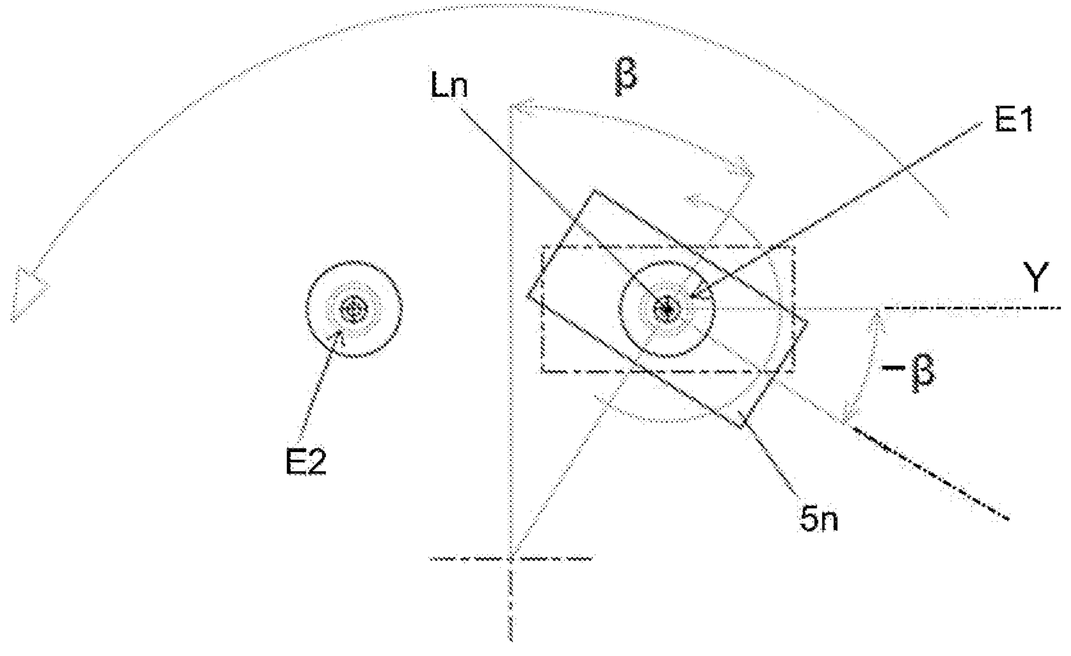
FIG. 7 is a schematic frontal representation of the equipment showing a condition of examining a (first) eye of a patient by an optical head or optical instrument of the equipment itself.

Considering then FIGS. 5 to 7, for the positioning of the first measuring head 51 on a first eye E1, based on the information received from the camera 8 (as mentioned, ΔZ and PD) the carousel 4 rotates around the rotation axis X' by an angle α and simultaneously moves along the height direction Z. In fact, for the positioning of its instrument axis L1 in exact coincidence with the ocular axis, it is necessary for the head or instrument 51 to perform a composite displacement, which takes into account the distance of the eye from the sagittal plane (which varies from subject to subject according to the measured PD value) and the positioning of the head in height, a displacement that can be schematized as shown in FIG. 6 according to a path Q from a point N1 to a point N2. Although this trajectory can be theoretically the result of the composition between a component of motion in laterality Y1 and a component of motion in height Z1, according to the invention, taking into account the angular component Ω2 resulting from the rotation α, it will be sufficient to add a component in height Z2.

It is therefore clear that with the arrangement according to the invention a displacement of the support of the carousel in the laterality direction Y is not needed to ensure the correct positioning; instead, it is made use of the height adjustment combined with the rotation. There entails the possibility of significant constructive simplification.

Since the optical heads, in order to work properly, may need to be positioned so that their development axis according to the direction of laterality Y is horizontal, the heads can be advantageously equipped with a system of rotation around their respective axis Ln, as shown in the diagram in FIG. 7, so as to recover the inclination β resulting from a given rotation of the carousel and the positioning on the first eye, through a counter-rotation of opposite sign (−β).

The eye makes natural movements during the examination and the device must be able to follow these movements to allow the measuring head or instrument to remain in the correct operating position. Thanks to an eye-tracking system, the coordinates of the eye are recorded in real time and sent to the control system, which in turn transmits the relative centering corrections to the driving units. Then, through micro-movements of rotation and height compensation, the measuring head remains correctly aligned with the eye to be examined.

Moreover, the measuring head must be positioned at the correct working distance in the focus condition in order to function properly. This is achieved by means of an autofocus system that sends command data to drive the displacement along the depth direction X. To reduce the positioning times along this depth direction X, the instruments or heads can be assembled on carousel 4 so that their focusing planes lie on the same plane, as shown in FIG. 8, where it can be seen that this condition is achieved with optimized mountings instrument-by-instrument, differentiating the distance X an between the same instrument and a frontal plane at the chin rest and rail region according to the focal characteristics of the instrument itself.

Having performed the examination with the first measurement head 51 one will proceed to measurements with the other heads as described above, with the carousel rotating by a (known) construction angle, possibly different from the angle α, depending on the angular distance separating the various heads or instruments.

For each of the optical heads 5*n* described above, a transition from the first to the second eye occurs (FIG. 9) by rotating the carousel by an angle δ such that the relative chord corresponds to the interpupillary distance recorded at the time of initial positioning. Also in this case, the combination of the rotational movement and the height adjustment determines a trajectory with a movement component according to the direction of laterality Y, without the need for the carousel support to make a shift in that direction. As again shown in FIG. 9, according to the above-mentioned embodiment, the head 5*n* can be rotated around its own optical axis Ln, by an angle δ able to maintain the condition of horizontality of its own axis in the laterality direction Y.

It will be easily appreciated how the advantageous aspects of the present disclosure make it possible to use a large number of different instruments, guaranteeing fast examination sessions, with a wide range of spatial adjustments, without interference between the various optical paths and with a rational distribution of weights and dimensions.

In addition to the number of devices or instruments, they can obviously vary in their type and nature, being able to create different devices with different combinations according to specific needs and intended use.

In particular, and by way of non-exhaustive and non-limiting example, the instruments or optical heads can be chosen from among:

Corneal topographer,
Topo-aberrometer,
Tomo-topographer (Scheimpflug camera with topographer)
Tomograph (Scheimpflug camera only)
Aberrometer
Air puff Tonometer
Fundus camera
Auto refractometer
Endothelial microscope.

The heads/instruments can, advantageously, be left functionally independent, but also integrated or otherwise made to cooperate through suitable circuitry and control systems.

The present invention has been described thus far with reference to its preferred embodiments. It is to be understood that there may be other forms of embodiments pertaining to the same inventive core, falling within the scope of protection of the attached claims.

The invention claimed is:

1. An ophthalmic apparatus comprising a plurality of optical devices including optical instruments, optical heads, or any combination thereof for measuring or evaluating a characteristic of an eye of a subject, each optical device of said plurality of optical devices having its own instrument optical axis, said plurality of optical devices being mounted on a frame comprising a base defining a resting plane for resting on a horizontal surface, and a carousel rotatable with respect to said frame about a carousel axis of rotation parallel to said resting plane, said plurality of optical devices being arranged on said carousel so that their respective instrument optical axes are parallel to said carousel axis of rotation, the apparatus comprising drive and control means, wherein: said carousel is supported by said frame so that said carousel axis of rotation is movable at least with respect to a height direction orthogonal to said resting plane; said control means being configured to perform a selective optical alignment of said plurality of optical devices with a patient's eye according to a laterality direction parallel to said resting plane and orthogonal to said rotation axis, by means of a position adjustment that combines a rotation of said carousel around said carousel axis of rotation and a displacement of said carousel axis along said height direction, wherein said carousel is supported by said frame such that said carousel axis of rotation is fixed to the frame with respect to said direction of laterality, and wherein one optical device of said plurality of optical devices is mounted on said carousel so as to be rotatable with respect thereto about said instrument optical axis of said one optical device relative to said carousel, wherein said one optical device is adapted to recover an inclination taken due to a corresponding rotation of the carousel about said carousel axis of rotation, by means of a counter-rotation of said one optical device about said instrument optical axis.

2. The apparatus according to claim 1, comprising chin rest means for supporting the head of the patient, movable in said height direction and controlled by said control means, and wherein at least one of said plurality of optical devices comprises image capturing and facial recognition means, said control means being configured to process the captured images to record the coordinates of both eyes of the patient according to the height direction and according to the laterality direction.

3. The apparatus according to claim 2, wherein said control means are apt to retrieve from said eye coordinates an interpupillary distance and a differential height of the eyes with respect to a reference mark provided on said chin rest means, and configured to determine, based on said interpupillary distance and said differential height, a fine-tuning displacement of said chin rest means, rotations of the carousel and displacements of the same in said height direction to align the instrument optical axes of said plurality of optical devices with the patient's eyes.

4. The apparatus according to claim 1, wherein said carousel is supported by said frame such that said carousel axis of rotation is also movable with respect to a depth direction (X) parallel to said resting plane and to said axis of rotation of said carousel.

5. The apparatus according to claim 4, wherein said frame comprises a column rising from a foot of said base and to which said carousel is pivotably connected, said column being movable with respect to said foot according to said height adjustment direction and depth adjustment direction.

6. The apparatus according to claim 1, wherein said plurality of optical devices are arranged in an unequally angularly spaced fashion along the periphery of said carousel.

7. The apparatus according to claim 1, wherein said plurality of optical devices are arranged in an equally angularly spaced fashion along the periphery of said carousel.

8. The apparatus according to claim 1, wherein said carousel has a circular periphery.

9. The apparatus according to claim 8, wherein said plurality of optical devices are arranged over a plane face of said carousel orthogonal with said carousel axis of rotation.

10. The apparatus according to claim 1, wherein said plurality of optical devices are selected from the group consisting of: corneal topographer; topo-aberrometer; tomo-topographer; tomograph; aberrometer; air puff tonometer; fundus camera; autorefractometer; and endothelial microscope.

11. The apparatus according to claim 1, wherein said plurality of optical devices are configured so as to be functionally independent from each other.

12. A method for optically aligning with a patient's eye an optical device of a plurality of optical devices of an ophthalmic apparatus, said plurality of optical devices comprising optical instruments, optical heads, or a combination thereof, each of the plurality of optical devices having its own instrument optical axis, said plurality of optical devices being mounted on a frame comprising a base defining a resting plane on a horizontal surface, and a carousel rotatable with respect to said frame about a carousel axis of rotation-parallel to said resting plane, said plurality of optical devices being arranged so that said instrument optical axes are parallel to said carousel axis of rotation, the apparatus comprising drive and control means, wherein: said carousel is supported by said frame so that said carousel axis of rotation is movable only with respect to a height direction orthogonal to said resting plane; the method providing to perform a selective optical alignment of one optical device of said plurality of optical devices with a patient's eye according to a lateral direction parallel to said resting plane and orthogonal to said axis of rotation, by means of a position adjustment of said one optical device that combines a rotation of said carousel about said carousel axis of rotation and a displacement of said carousel axis of rotation along said height direction, and wherein said one optical device is rotated with respect to said carousel about said instrument optical axis of said one optical device, recovering an inclination taken due to a corresponding rotation of the carousel about said carousel axis of rotation, by means of a counter-rotation of said one optical device about said instrument optical axis.

* * * * *